United States Patent
Pasquet et al.

(10) Patent No.: US 6,399,050 B1
(45) Date of Patent: Jun. 4, 2002

(54) HAIR COSMETIC COMPOSITION IN THE FORM OF A WATER-IN-SILICONE EMULSION COMPRISING AT LEAST ONE FIXING POLYMER

(75) Inventors: Dorothée Pasquet, Bois Colombes; Emmanuelle Belli, Paris, both of (FR)

(73) Assignee: L'Oreal S.A., Paris (FR)

( * ) Notice: Subject to any disclaimer, the term of this patent is extended or adjusted under 35 U.S.C. 154(b) by 19 days.

(21) Appl. No.: 09/598,414

(22) Filed: Jun. 19, 2000

(30) Foreign Application Priority Data

Jun. 18, 1999 (FR) .............................. 99 07769

(51) Int. Cl.$^7$ ................................ A61K 7/06
(52) U.S. Cl. ................. 424/70.12; 424/70.1; 424/70.11
(58) Field of Search ............................ 424/70.1, 70.11, 424/70.12

(56) References Cited

U.S. PATENT DOCUMENTS

| | | | |
|---|---|---|---|
| 2,047,398 A | 7/1936 | Voss et al. |
| 2,723,248 A | 11/1955 | Wright |
| 3,836,537 A | 9/1974 | Boerwinkle et al. |
| 3,925,542 A | 12/1975 | Viout et al. |
| 3,946,749 A | 3/1976 | Papantoniou |
| 3,966,403 A | 6/1976 | Papantoniou et al. |
| 3,966,404 A | 6/1976 | Papantoniou et al. |
| 4,031,307 A | 6/1977 | DeMartino et al. |
| 4,128,631 A | 12/1978 | Lundmark et al. |
| 4,137,208 A | 1/1979 | Elliott |
| 4,165,367 A | 8/1979 | Chakrabarti |
| 4,282,203 A | 8/1981 | Jacquet et al. |
| 4,311,695 A | 1/1982 | Starch |
| 4,693,935 A | 9/1987 | Mazurek |
| 4,728,571 A | 3/1988 | Clemens et al. |
| 4,931,062 A | 6/1990 | Bay et al. |
| 4,972,037 A | 11/1990 | Garbe et al. |
| 5,538,717 A | 7/1996 | La Poterie |
| 6,039,933 A | 3/2000 | Samain et al. |
| 6,042,819 A | 3/2000 | Karien et al. |
| 6,060,044 A | 5/2000 | Cretois et al. |
| 6,071,499 A | 6/2000 | Dupuis |
| 6,214,319 B1 * | 4/2001 | Franzke et al. |

FOREIGN PATENT DOCUMENTS

| | | |
|---|---|---|
| DE | 23 30 956 | 1/1974 |
| DE | 42 29 922 | 3/1994 |
| DE | 196 42 622 | 4/1998 |
| EP | 0 080 976 | 6/1983 |
| EP | 0 260 641 | 3/1988 |
| EP | 0 407 089 A2 * | 1/1991 |
| EP | 0 412 704 | 2/1991 |
| EP | 0 412 707 | 2/1991 |
| EP | 0 582 152 | 2/1994 |
| EP | 0 619 111 | 10/1994 |
| EP | 0 637 600 | 2/1995 |
| EP | 0 648 485 | 4/1995 |
| EP | 0 656 021 | 6/1995 |
| EP | 0 751 162 | 1/1997 |
| EP | 0 761 214 | 3/1997 |
| FR | 1 222 944 | 6/1960 |
| FR | 1 400 366 | 4/1965 |
| FR | 1 564 110 | 4/1969 |
| FR | 1 580 545 | 9/1969 |
| FR | 2 077 143 | 10/1971 |
| FR | 2 265 781 | 10/1975 |
| FR | 2 265 782 | 10/1975 |
| FR | 2 350 384 | 12/1977 |
| FR | 2 357 241 | 2/1978 |
| FR | 2 393 573 | 1/1979 |
| FR | 2 439 798 | 5/1980 |
| FR | 2 743 297 | 7/1997 |
| FR | 2 745 173 | 8/1997 |
| GB | 0 839 805 | 6/1960 |
| WO | WO 93/23009 | 11/1993 |
| WO | WO 93/23446 | 11/1993 |
| WO | WO 94/03510 | 2/1994 |
| WO | WO 95/00578 | 1/1995 |
| WO | WO 97/33554 | 9/1997 |
| WO | WO 98/38970 | 9/1998 |
| WO | WO2001028506 * | 4/2001 |

OTHER PUBLICATIONS

English language Derwent Abstract of DE 42 29 922, (1994).
English language Derwent Abstract of DE 196 42 622, (1998).
English language Derwent Abstract of EP 0 080 976, (1983).
English language Derwent Abstract of EP 0 637 600, (1995).
English language Derwent Abstract of EP 0 656 021, (1995).
English language Derwent Abstract of EP 0 751 162, (1997).
English language Derwent Abstract of FR 1 564 110, (1969).
English language Derwent Abstract of FR 2 077 143, (1971).
English language Derwent Abstract of FR 2 357 241, (1978).
English language Derwent Abstract of FR 2 745 297, (1997).
English language Derwent Abstract of FR 2 745 173, (1997).

* cited by examiner

Primary Examiner—Thurman K. Page
Assistant Examiner—Brian K. Seidleck
(74) Attorney, Agent, or Firm—Finnegan, Henderson, Farabow, Garrett & Dunner, LLP

(57) ABSTRACT

The invention relates to a hair cosmetic composition in the form of a water-in-silicone emulsion comprising in a cosmetically acceptable medium: (i) at least one non-oxyalkylenated silicone chosen from linear and cyclic, volatile and non-volatile, and arylated and non-arylated silicones, wherein the total non-oxyalkylenated silicone is more than 10% by weight with respect to the total weight of the composition; (ii) at least one emulsifying oxyalkylenated silicone; and (iii) at least one anionic, cationic, amphoteric, or non-ionic fixing polymer. The invention also relates to the inclusion of the hair cosmetic composition in the manufacture of hair formulations, such as care products, conditioners, or products for fixing and/or retaining the form of the hair.

35 Claims, No Drawings

HAIR COSMETIC COMPOSITION IN THE FORM OF A WATER-IN-SILICONE EMULSION COMPRISING AT LEAST ONE FIXING POLYMER

The subject-matter of the invention is a hair cosmetic composition in the form of a water-in-silicone emulsion comprising at least one fixing polymer. The invention is also targeted at the application of the hair cosmetic composition in the manufacture of hair formulations, such as care products, conditioning products, or products for fixing and/or retaining the form of the hair.

Hair cosmetic compositions generally comprise at least one polymer, preferably an anionic, non-ionic, or amphoteric polymer. They can, for example, contribute fixing properties to the hair.

The most commonly used formulations are generally provided in the form of an aerosol mousse, of an aerosol spray, of a pump-action spray, or else of a gel.

Mousses generally make it possible to obtain good distribution of the cosmetic compositions over the hair and they are, in addition, easy to use. As the polymers used in these products are generally non-foaming or weakly foaming, it is necessary to add a foaming agent and/or an agent, which improves the quality of the mousse.

The foaming agents and/or agents, which improve the quality of the mousse, commonly used are, for example, anionic, non-ionic, or amphoteric surface-active agents. However, these surface-active agents sometimes bring about refoaming on wet hair, which is detrimental to rapid and careful styling of the hair.

Furthermore, the application of mousse to the hair sometimes exhibits the disadvantage of rendering the hairstyle lank. Finally, the preparation of mousses necessarily requires an aerosol device.

Aerosol sprays make possible the fast and homogeneous distribution of the product over the hair and provide, for example, very good qualities of form retention and of hold of the hairstyle. However, they sometimes exhibit the disadvantage of giving a sticky feel on application and a rough feel after drying; their cosmetic qualities are limited. Furthermore, they require, just like mousses, the use of an aerosol device.

Among the documents of the prior art disclosing hair cosmetic compositions, which are provided in particular in the form of mousses or sprays, the document EP 260,641, incorporated herein by reference, discloses emulsions comprising 0.1 to 5% by weight of a dimethylpolysiloxane/polyoxyalkylene copolymer having a cloud point of ranging from 20 to 40° C., 0.05 to 10% of a silicone oil, and 0.1 to 10% of a fixing polymer, which is soluble in water or a mixture of water and alcohol, as well as ionic or non-ionic surface-active agents, in a water/alcohol mixture.

Gels are another galenic form commonly used to contribute, for example, effective form retention to the hairstyle by virtue of the polymers of which they comprise. However, some disadvantages are observed, such as a texture, which confers lankness on application (due to the presence of some thickeners), a sticky feel, a hairstyle that is not very natural, and a lack of softness.

The Inventors have discovered, surprisingly and unexpectedly, contrary to all expectations, that it is possible to prepare hair cosmetic compositions, which can have fewer of the disadvantages expressed above, by choosing, as a cosmetic vehicle, a specific emulsion of water and of silicone, which will be defined in detail subsequently.

The subject-matter of the invention is a hair cosmetic composition in the form of a water-in-silicone emulsion comprising in a cosmetically acceptable medium:

(i) at least one non-oxyalkylenated silicone chosen from linear and cyclic, volatile and non-volatile, and arylated and non-arylated silicones, wherein the total non-oxyalkylenated silicone is more than 10% by weight with respect to the total weight of the composition;
(ii) at least one emulsifying oxyalkylenated silicone; and
(ii) at least one anionic, cationic, amphoteric, or non-ionic fixing polymer.

Another subject-matter of the invention is a hair cosmetic process employing this composition.

Another subject-matter of the invention is more particularly a process for fixing and/or maintaining the form of the hair employing this composition.

Yet another subject-matter of the invention is the use of this composition in the manufacture of hair products, in particular those intended for the fixing and/or shaping of the hairstyle.

Within the meaning of the present invention, the term "water-in-silicone emulsion" is understood to mean a dispersion with non-continuous phase formed by an aqueous phase and a continuous phase formed by a fatty phase, the continuous phase being mainly composed of the said silicone.

The hair cosmetic compositions in accordance with the present invention advantageously exhibit a viscosity, measured by means of a Rheomat RM 180 at 25° C. with reading after 30 seconds, of greater than 5 ps and more advantageously still of greater than 10 ps, at a shear rate of 200 s$^{-1}$.

Within the meaning of the present invention, the term "non-oxyalkylenated silicone" is understood to mean any organosilicone polymer or oligomer with a branched or crosslinked and linear or cyclic structure of variable molecular weight obtained by polymerization and/or polycondensation of suitably functionalized silanes and essentially composed of a repetition of main units in which the silicon atoms are connected to one another via oxygen atoms with the formation of a siloxane bond ≡Si—O—Si≡, optionally substituted hydrocarbonaceous radicals being directly bonded from a carbon atom to the said silicon atoms. The most common hydrocarbonaceous radicals are alkyl radicals, especially $C_1$–$C_{10}$ alkyl radicals in particular methyl radicals, fluoroalkyl radicals, and aryl radicals in particular phenyl radicals. Such non-oxyalkenated silicones are, for example, sold under the trade name DC 1501 Fluid by the company Dow Corning.

The non-oxyalkylenated silicones can be modified, for example by carboxyl groups.

It is possible, for example, to use non-oxyalkylenated silicone with a carboxyl functional group corresponding to the formula II':

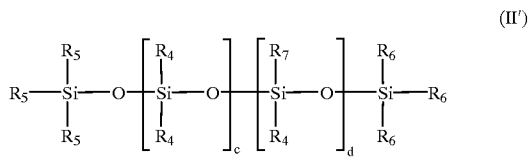

(II')

in which the $R_4$ radicals are identical or different and are chosen from linear and branched $C_1$–$C_{22}$ alkyl radicals, $C_1$–$C_{22}$ alkoxy radicals, carboxyl radicals, and phenyl radicals; the $R_5$, $R_6$, and $R_7$ radicals are identical or different and are chosen from linear and branched $C_1$–$C_{22}$ alkyl radicals, $C_1$–$C_{22}$ alkoxy radicals, and carboxyl radicals; c and d are numbers ranging from 0 to 1000; and the sum c+d preferably ranging from 2 to 1000, wherein at least one of the $R_4$, $R_5$, $R_6$, and $R_7$ radicals is a carboxyl radical.

Use is advantageously made of the products sold under the trade name Oil M 642, SLM 23 000/1, or SLM 23 000/2 by the company Wacker, under the trade name 176-12057 by the company General Electric, under the trade name FZ 3703 by the company OSI, or under the trade name BY 16 880 by the company Toray Silicone.

Preferably, the number-average molecular weight of the silicone polymer ranges from 10,000 to 1,000,000 approximately and more preferably still from 10,000 to 100,000 approximately.

Other non-oxyalkylenated silicones, which are particularly well suited to the implementation of the present invention, are silicones comprising at least one substituent that comprises at least two identical or different groups chosen from carboxylic acids or their salts, amides, and esters. At least one of these groups is a carboxylic acid or its salts.

These silicones preferably comprise at least one unit of formula IV':

$$ZR_aSiO_{(3-a)/2} \quad (IV')$$

in which the R radicals are identical or different and are chosen from alkyl radicals especially $C_1$–$C_{10}$ alkyl radicals and in particular methyl radicals, fluoroalkyl radicals especially $C_1$–$C_{10}$ fluoroalkyl radicals, or $C_6$–$C_{12}$ aryl radicals and in particular phenyl radicals; a is chosen from 0, 1, and 2 and preferably 1 or 2; and Z is a radical corresponding to the following formula V':

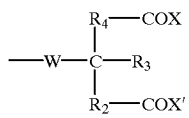

$$(V')$$

in which W, $R_2$, and $R_4$, which are identical or different, are chosen from a covalent bond and linear and branched alkylene radicals having from 1 to 6 carbon atoms, which can comprise a hydroxyl group; $R_3$ is a radical chosen from a hydrogen atom and linear and branched $C_1$–$C_6$ alkyl radicals; X and X', which are identical or different, are radicals chosen from the OM, $NR_5R_6$, and $OR_7$ radicals; M denotes a hydrogen atom, an alkali metal (for example, $Na^+$ or $K^+$), $NH_4^+$ or ammonium groups comprising a residue chosen from basic amino acids such as lysine, arginine, sarcosine, ornithine, or citrulline, and aminoalcohols such as monoethanolamine, diethanolamine, triethanolamine, glucamine, N-methylglucamine, or 3-amino-1,2-propanediol; $R_5$ and $R_6$, which are identical or different, are radicals chosen from hydrogen and linear and branched $C_1$–$C_6$ alkyl radicals or else $R_5$ and $R_6$ can together form a 5- or 6-membered heterocycle, such as morpholine; $R_7$ is a radical chosen from linear and branched $C_1$–$C_{30}$ alkyl radicals; and at least one of the X and X' groups denotes OM.

The other units of the silicone are preferably chosen from those of formula VI':

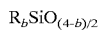

$$R_bSiO_{(4-b)/2} \quad (VI')$$

in which R has the same meaning as for the formula IV' and b is equal to 0, 1, 2, or 3 and preferably equal to 2 or 3.

Silicones comprising at least one unit of formula IV' are disclosed in particular in U.S. Pat. No. 4,931,062, incorporated herein by reference. Such silicones are, for example, sold under the trade name SLM 23 105 by the company Wacker and under the trade name Densodrin OF by the company BASF.

The term "volatile silicone" is understood to mean, according to the present invention, any silicone exhibiting a measurable vapour pressure and in particular a vapour pressure which, measured at 25° C. at atmospheric pressure ($10^5$ Pa), is preferably greater than 0.01 mm Hg (2.6 Pa). Use is preferably made of oils with a boiling point at atmospheric pressure of the order of 80 to 260° C.

Mention may be made, among volatile silicones, of:

(i) cyclic volatile silicones having from 3 to 7 silicon atoms and preferably from 4 to 5 silicon atoms, which can correspond to the following formula (VIII):

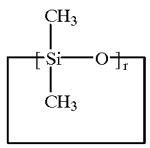

(VIII)

in which r varies from 3 to 7 inclusive.

Examples include cyclotetradimethylsiloxane, cyclopentadimethylsiloxane, or cyclohexadimethylsiloxane.

(ii) linear volatile silicones having from 2 to 9 silicon atoms. They can correspond to the following formula (IX):

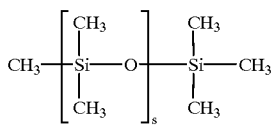

(IX)

in which s varies from 1 to 8 inclusive.

Examples include hexamethyldisiloxane or octamethyltrisiloxane.

The volatile silicones are preferably cyclotetradimethylsiloxane and hexamethyldisiloxane.

The term "non-volatile silicone" is understood to mean, according to the present invention, any silicone exhibiting a vapour pressure, measured at 25° C. at atmospheric pressure ($10^5$ Pa), preferably of less than 0.01 mm Hg (2.6 Pa).

The non-volatile silicones may or may not be modified. Use may be made, among unmodified silicones, of, for example, silicone oils, gums, or resins.

Non-volatile arylated silicones comprise at least one optionally substituted radical of aryl type. The aryl radicals are, for example, phenyl, naphthyl, benzyl, or phenethyl.

The non-volatile arylated silicones preferably exhibit the following formula (X):

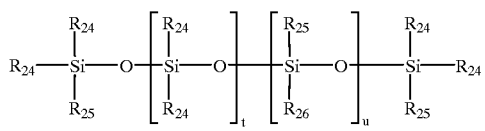

(X)

in which $R_{24}$, which is identical or different, denotes a $C_1$–$C_{10}$ alkyl radical; $R_{26}$, which is identical or different, denotes an aryl group, it being possible for this aryl group to comprise one or more optionally substituted aryl rings; $R_{25}$, which is identical or different, denotes $R_{26}$, $R_{24}$, or $Si(R_{24})_3$; t varies from 0 to 1000; u varies from 1 to 1000; and the sum t+u can vary from 1 to 2000. Herein, the term "alkyl radical" encompasses linear, branched, and cyclic radicals.

The substituents of the aryl groups can be alkyl, alkenyl, acyl, ketone, halogen (for example, Cl and Br), or amine groups. Examples of aryl groups are phenyl, a phenyl group substituted by $C_1$–$C_5$ alkyl radicals or $C_1$–$C_5$ alkenyl radicals such as allylphenyl, methylphenyl, ethylphenyl, or vinylphenyl, and their mixtures.

$R_{24}$ preferably denotes a methyl radical. $R_{26}$ preferably denotes a phenyl radical. $R_{25}$ preferably denotes a methyl, phenyl, or trimethylsilyl radical. More particularly, the sum t+u varies from 1 to 1000.

Use may be made, among the compounds of formulae (X), of, for example, phenyl trimethicone, diphenyl dimethicone, or phenyl dimethicone (INCI names, 5th edition, 1993).

Mention may be made, as example of these compounds, of those sold by the company Bayer under the name Baysilone Fluid PD5 Oil, by the company Dow Corning under the name Dow Corning 556 Fluid, by Rhône-Poulenc under the names Mirasil DPDM, Rhodorsil Oil 510 V 100, Rhodorsil Oil 550, Rhodorsil Oil 510V500, or Rhodorsil Oil 710, or by the company Wacker under the name Wacker Belsil PDM 20, PDM 200, or PDM 100.

Use may also be made, as arylated silicone, of a silicone comprising at least one aryl group, such as polyphenylmethylsiloxane or polydimethyldiphenylsiloxane oils.

The arylated silicones particularly targeted by the present invention are those disclosed in French Patent FR 2,745,173, incorporated herein by reference.

The arylated silicones used in accordance with the invention are in particular the polyalkylarylsiloxane oils of the type of those described in the Kirk-Othmer Encyclopaedia, 4th ed., Vol. 22.

Mention may be made, as another type of non-oxyalkylenated modified silicone, of those modified by alkoxylated or sulphonate or thiol or hydroxylated or aminated or hydroxyacylamino groups. The non-oxyalkylenated silicone will preferably be chosen from volatile silicones, non-volatile arylated silicones, and silicones with carboxyl groups.

The preferred polyalkylarylsiloxane oils are polydimethyldiphenylsiloxane oils and polyphenylmethylsiloxane oils.

Mention may be made, by way of example, of the polydimethyldiphenyl-siloxane oils sold by the company Rhône-Poulenc under the trade name Silbione and the polyphenylmethylsiloxane oils sold by the company Goldschmidt under the trade name Abil AV20-200-350-1000. Mention may also be made of the phenylated silicone sold by Dow Corning under the trade name DC 556.

In accordance with the invention, the emulsifying oxyalkylenated silicones are preferably chosen from the compounds of general formula (I):

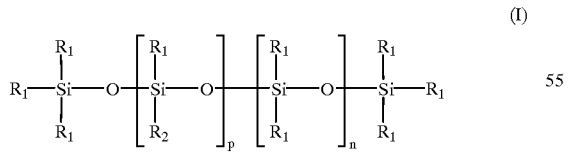

(I)

in which $R_1$, which is identical or different, is a radical chosen from a hydrogen atom, linear and branched $C_1$–$C_{30}$ alkyl radicals, and a phenyl radical; $R_2$, which is identical or different, represents —$(C_xH_{2x})$—$(OC_2H_4)_a$—$(OC_3H_6)_b$—$OR_3$; $R_3$, which is identical or different, is a radical chosen from a hydrogen atom, linear and branched alkyl radicals having from 1 to 12 carbon atoms, and linear and branched acyl radicals having from 2 to 12 carbon atoms; n varies from 0 to 1000; p varies from 1 to 8; a varies from 0 to 50; b varies from 0 to 50; a+b is greater than or equal to 1; x varies from 1 to 5; and the number-average molecular weight being greater than or equal to 15,000 and preferably ranges from 25,000 to 75,000.

Use is preferably made of the oxyalkylenated silicones of general formula (I), which meet at least one and preferably all of the following conditions: $R_1$ denotes the methyl radical; $R_3$ is a radical chosen from a hydrogen atom, a methyl radical, an acetyl radical, and preferably a hydrogen; p varies from 2 to 6; a is varies from 5 to 40 and preferably from 15 to 30; b varies from 5 to 40 and preferably from 15 to 30; x is equal to 2 or 3; and n varies from 20 to 600 preferably from 50 to 500 and more particularly still from 200 to 500.

Such silicones are, for example, disclosed in U.S. Pat. No. 4,311,695, which is incorporated by way of reference.

The most particularly preferred silicones are, for example, those sold as a 10% by weight solution in a cyclomethicone (Dow Corning 344) under the trade name Fluid DC 3225 C by the company Dow Corning or that sold under the name Silwet L 7001 by the company Union Carbide.

The cationic, anionic, amphoteric, and non-ionic fixing polymers, which can be used in accordance with the invention are described hereinbelow.

The cationic fixing polymers, which can be used according to the present invention, are preferably chosen from polymers comprising primary, secondary, tertiary, and/or quaternary amine groups forming part of the polymer chain or directly bonded to the latter and having a molecular weight ranging from 500 to approximately 5,000,000 and preferably from 1000 to 3,000,000.

Mention may more particularly be made, among these polymers, of the following cationic fixing polymers:

(1) homopolymers or copolymers derived from acrylic or methacrylic esters or amides comprising at least one of the units of following formulae:

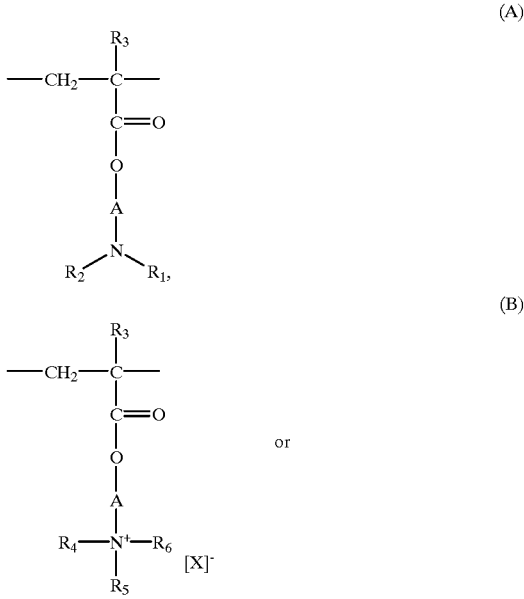

-continued

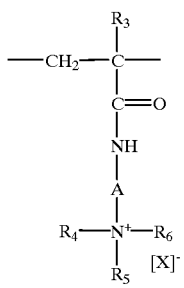

(C)

in which $R_3$ denotes a hydrogen atom or a $CH_3$ radical; A denotes linear and branched alkyl groups comprising 1 to 6 carbon atoms or hydroxyalkyl groups comprising 1 to 4 carbon atoms; $R_4$, $R_5$, and $R_6$, which are identical or different, are radicals chosen from an alkyl group having from 1 to 18 carbon atoms and a benzyl radical; $R_1$ and $R_2$ are radicals chosen from hydrogen and an alkyl group having from 1 to 6 carbon atoms; and X denotes a methyl sulphate anion or a halide, such as chloride or bromide.

The copolymers of the family (1) additionally comprise one or more units derived from comonomers, which can be chosen from the family of acrylamides, methacrylamides, diacetone acrylamides, acrylamides and methacrylamides substituted on the nitrogen by lower alkyls, acrylic or methacrylic acids or their esters, vinyllactams such as vinylpyrrolidone or vinyl-caprolactam, or vinyl esters.

Thus, mention may be made, among these copolymers of the family (1), of:

copolymers of acrylamide and of dimethylaminoethyl methacrylate quaternized with dimethyl sulphate or with a dimethyl halide, such as that sold under the name Hercofloc by the company Hercules, copolymers of acrylamide and of methacryloyloxyethyl-trimethylammonium chloride which is disclosed, for example, in Patent Application EP-A-080,976, incorporated hereby by reference, and are sold under the name Bina Quat P 100 by the company Ciba-Geigy, the copolymer of acrylamide and of methacryloyloxyeth-yltrimethylammonium methyl sulphate sold under the name Reten by the company Hercules, optionally quaternized vinylpyrrolidone/dialkyl-aminoalkyl acrylate or methacrylate copolymers, such as the products sold under the name "Gafquat" by the company ISP, such as, for example, "Gafquat 734" or "Gafquat 755", or else the products named "Copolymer 845, 958 and 937". These polymers are disclosed in detail in French Patents 2,077,143 and 2,393,573, both of which are incorporated herein by reference.

dimethylaminoethyl methacrylate/vinylcaprolactam/vinylpyrrolidone terpolymers, such as the product sold under the name Gaffix VC 713 by the company ISP, and the quaternized dimethylaminopropyl methacrylamide/vinylpyrrolidone copolymer, such as the product sold under the name "Gafquat HS 100" by the company ISP.

(2) quaternized polysaccharides, disclosed more particularly in U.S. Pat. No. 4,031,307, incorporated herein by reference, such as guar gums comprising cationic tri-alkylammonium groups.

Such products are sold in particular under the trade names Jaguar C13 S, Jaguar C 15 and Jaguar C 17 by the company Meyhall.

(3) quaternary copolymers of vinylpyrrolidone and of vinylimidazole, such as the products sold by BASF under the name Luviquat TFC.

(4) chitosans or their salts. The salts, which can be used, are in particular chitosan acetate, lactate, glutamate, gluconate, or pyrrolidone-carboxylate.

Mention may be made, among these compounds, of the chitosan having a degree of deacetylation of 90.5% by weight sold under the name Kytan Crude Standard by the company Aber Technologies or the chitosan pyrrolidone-carboxylate sold under the name Kytamer PC by the company Amerchol.

(5) cationic cellulose derivatives, such as copolymers of cellulose or of cellulose derivatives grafted with a water-soluble monomer comprising a quaternary ammonium, which are disclosed in particular in U.S. Pat. No. 4,131,576, incorporated herein by reference, such as hydroxyalkyl celluloses, for example hydroxymethyl, hydroxyethyl or hydroxypropyl celluloses, grafted in particular with a methacryloyloxyethyltrimethylammonium, methacrylamidopropyltrimethylammonium, or dimeth-yldiallylammonium salt.

The commercial products corresponding to this definition are more particularly the products sold under the name "Celquat L 200" and "Celquat H 100" by the company National Starch.

The anionic fixing polymers generally used are polymers comprising groups derived from carboxylic, sulphonic, or phosphoric acid and have a molecular weight ranges from approximately 500 to 5,000,000.

1) The carboxyl groups are contributed by unsaturated carboxylic mono- or diacid monomers such as those corresponding to the formula:

(II)

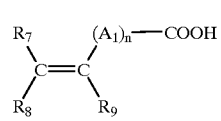

in which n is an integer from 0 to 10; $A_1$ denotes a methylene group and when n is greater than 1, each $A_1$ is represented by —$LCH_2$—, where L is a heteroatom, such as oxygen or sulphur; $R_7$ is a radical chosen from a hydrogen atom, a phenyl group, and a benzyl group; $R_8$ is a radical chosen from a hydrogen atom, a lower alkyl group, and a carboxyl group; and $R_9$ is a radical chosen from a hydrogen atom, a lower alkyl group, a —$CH_2$—COOH, a phenyl group, and a benzyl group.

In the abovementioned formula, a lower alkyl radical preferably denotes a group having 1 to 4 carbon atoms and in particular methyl and ethyl.

The preferred anionic fixing polymers comprising carboxyl groups according to the invention are:

(A) Homo- or copolymers of acrylic or methacrylic acid or their salts and in particular the products sold under the names Versicol E or K by the company Allied Colloid and Ultrahold by the company BASF. The copolymers of acrylic acid and of acrylamide sold in the form of their sodium salt under the names Reten 421, 423, or 425 by the company Hercules or the sodium salts of polyhydroxycarboxylic acids.

(B) Copolymers of acrylic acid or methacrylic acid with a monoethylenic monomer, such as ethylene, styrene, vinyl esters, or esters of acrylic or methacrylic acid, optionally grafted onto a polyalkylene glycol, such as polyethylene glycol, and optionally crosslinked. Such polymers are disclosed in particular in French Patent 1,222,944 and German Application 2,330,956 both of which are incorporated herein by reference, the copolymers of this type comprising, in their chain, an optionally N-alkylated and/or -hydroxyalkylated acrylamide unit, such as disclosed in particular in Luxembourgian Patent Applications 75370 and 75371 both of which are incorporated herein by reference or provided under the name Quadramer by the company American Cyanamid. Mention may also be made of copolymers of acrylic acid and of $C_1$–$C_4$ alkyl methacrylate and terpolymers of vinylpyrrolidone, of acrylic acid, and of $C_1$–$C_{20}$ alkyl methacrylate for example lauryl methacrylate, such as that sold by the company ISP under the name Acrylidone LM, and methacrylic acid/ethyl acrylate/tert-butyl acrylate terpolymers, such as the product sold under the name Luvimer 100 P by the company BASF.

(C) copolymers derived from crotonic acid, such as those comprising, in their chain, vinyl acetate or propionate units and optionally other monomers, such as allyl or methallyl esters, vinyl ether or vinyl ester of a linear or branched saturated carboxylic acid comprising a long hydrocarbon chain, such as those comprising at least 5 carbon atoms, it optionally being possible for these polymers to be grafted and crosslinked, or alternatively a vinyl, allyl, or methallyl ester of an α- or β-cyclic carboxylic acid. Such polymers are disclosed, inter alia, in French Patents 1,222,944, 1,580,545, 2,265,782, 2,265,781, 1,564,110, and 2,439,798 all of which are incorporated herein by reference. Commercial products coming within this class are the Resins 28-29-30, 26-13-14 and 28-13-10 sold by the company National Starch.

(D) copolymers derived from $C_4$–$C_8$ monounsaturated carboxylic acids or anhydrides chosen from:

copolymers comprising (i) one or more maleic, fumaric, or itaconic acids or anhydrides and (ii) at least one monomer chosen from vinyl esters, vinyl ethers, vinyl halides, phenylvinyl derivatives, or acrylic acid and its esters, the anhydride functional groups of these copolymers optionally being monoesterified or monoamidated; such polymers are disclosed in particular in U.S. Pat. Nos. 2,047,398 and 2,723,248, and Patent GB 839,805 all of which are incorporated herein by reference and in particular those sold under the names Gantrez AN or ES by the company ISP.

copolymers comprising (i) one or more maleic, citraconic, or itaconic anhydrides and (ii) one or more monomers chosen from allyl or methallyl esters, optionally comprising one or more acrylamide, methacrylamide, α-olefin, acrylic or methacrylic ester, acrylic or methacrylic acid, or vinylpyrrolidone groups in their chain.

The anhydride functional groups of these copolymers optionally being monoesterified or monoamidated.

These polymers are, for example, disclosed in French Patents 2,350,384 and 2,357,241 which are incorporated herein by reference.

(E) polyacrylamides comprising carboxylate groups.

2) The polymers comprising sulpho groups are polymers comprising vinylsulphonic, styrenesulphonic, naphthalenesulphonic, or acrylamidoalkylsulphonic units derived from sulfonic acid.

These polymers can in particular be chosen from:

salts of polyvinylsulphonic acid having a molecular weight that ranges from approximately 1000 to 100,000, as well as copolymers with an unsaturated comonomer, such as acrylic or methacrylic acids and their esters as well as acrylamide or its derivatives, vinyl ethers, and vinylpyrrolidone.

salts of polystyrenesulphonic acid, the sodium salts having a molecular weight of approximately 500,000 and of approximately 100,000 sold respectively under the names Flexan 500 and Flexan 130 by National Starch. These compounds are disclosed in Patent FR 2,198,719 incorporated herein by reference.

salts of polyacrylamidesulphonic acids, including those mentioned in U.S. Pat. No. 4,128,631, incorporated herein by reference, and more particularly the polyacrylamidoethylpropanesulphonic acid sold under the name Cosmedia Polymer HSP 1180 by Henkel.

According to the invention, the anionic fixing polymers are preferably chosen from acrylic acid copolymers, such as the acrylic acid/ethyl acrylate/N-tert-butylacrylamide terpolymer sold under the name Ultrahold Strong by the company BASF; copolymers derived from crotonic acid, such as the vinyl acetate/vinyl tert-butylbenzoate/crotonic acid terpolymers and the crotonic acid/vinyl acetate/vinyl neododecanoate terpolymers sold under the name Resin 28-29-30 by the company National Starch; polymers derived from maleic, fumaric, or itaconic acids or anhydrides with vinyl esters, vinyl ethers, vinyl halides, phenylvinyl derivatives, or acrylic acid and its esters, such as the monoesterified methyl vinyl ether/maleic anhydride copolymer sold under the name Gantrez ES 425 by the company ISP; copolymers of methacrylic acid and of methyl methacrylate sold under the name Eudragit L by the company Rohm Pharma; the copolymer of methacrylic acid and of ethyl acrylate sold under the name Luvimer MAEX or MAE by the company BASF; the vinyl acetate/crotonic acid copolymer sold under the name Luviset CA 66 by the company BASF; and the vinyl acetate/crotonic acid copolymer grafted by polyethylene glycol sold under the name Aristoflex A by the company BASF.

The most particularly preferred anionic fixing polymers are chosen from the monoesterified methyl vinyl ether/maleic anhydride copolymer sold under the name Gantrez ES 425 by the company ISP; the acrylic acid/ethyl acrylate/N-tert-butylacrylamide terpolymer sold under the name Ultrahold Strong by the company BASF; the copolymers of methacrylic acid and of methyl methacrylate sold under the name Eudragit L by the company Rohm Pharma; the vinyl acetate/vinyl tert-butylbenzoate/crotonic acid terpolymers and the crotonic acid/vinyl acetate/vinyl neododecanoate terpolymers sold under the name Resin 28-29-30 by the company National Starch; the copolymer of methacrylic acid and of ethyl acrylate sold under the name Luvimer MAEX or MAE by the company BASF; and the vinylpyrrolidone/acrylic acid/lauryl methacrylate terpolymer sold under the name Acrylidone LM by the company ISP.

The amphoteric fixing polymers which can be used in accordance with the invention can be chosen from polymers comprising X and Y units distributed randomly in the polymer chain, where X denotes a unit derived from a monomer comprising at least one basic nitrogen atom and Y denotes a unit derived from an acidic monomer comprising one or more carboxyl or sulpho groups or else X and Y can denote groups derived from zwitterionic carboxybetaine or sulphobetaine monomers; X and Y can also denote a cationic polymer chain comprising primary, secondary, tertiary, or quaternary amine groups, in which at least one of the amine groups carries a carboxyl or sulpho group connected via a hydrocarbon radical, or else X and Y form part of a chain of a polymer comprising an α, β-dicarboxyethylene unit, one of the carboxyl groups of which has been reacted with a polyamine comprising one or more primary or secondary amine groups.

The most particularly preferred amphoteric fixing polymers corresponding to the definition given above are chosen from the following polymers:

(1) polymers resulting from the copolymerization of a monomer derived from a vinyl compound carrying a carboxyl group, particularly acrylic acid, methacrylic acid, maleic acid, or α-chloracrylic acid, and of a basic monomer derived from a substituted vinyl compound comprising at least one basic atom, particularly dialkylaminoalkyl methacrylate and acrylate or dialkylaminoalkylmethacrylamide and -acrylamide. Such compounds are disclosed in U.S. Pat. No. 3,836,537, incorporated herein by reference.

(2) polymers comprising units derived:
a) from at least one monomer chosen from acrylamides or methacrylamides substituted on the nitrogen by an alkyl radical,
b) from at least one acidic comonomer comprising one or more reactive carboxyl groups, and
c) from at least one basic comonomer, such as esters comprising primary, secondary, tertiary, and quaternary amine substituents of acrylic and methacrylic acids and the quaternization product of dimethylaminoethyl methacrylate with dimethyl or diethyl sulphate.

The more particularly preferred N-substituted acrylamides or methacrylamides according to the invention are the groups in which the alkyl radicals comprise from 2 to 12 carbon atoms and more particularly N-ethylacrylamide, N-tert-butylacrylamide, N-tert-octylacrylamide, N-octylacrylamide, N-decylacrylamide, N-dodecylacrylamide, and the corresponding methacrylamides.

The acidic comonomers are more particularly chosen from acrylic, methacrylic, crotonic, itaconic, maleic, or fumaric acids and alkyl monoesters having 1 to 4 carbon atoms of maleic or fumaric acids or anhydrides. The preferred basic comonomers are aminoethyl, butylaminoethyl, N,N'-dimethylaminoethyl, or N-tert-butylaminoethyl methacrylates.

Use is particularly made of the copolymers for which the CTFA name (4th Ed., 1991) is octylacrylamide/acrylates/butylaminoethyl methacrylate copolymer, such as the products sold under the name Amphomer or Lovocryl 47 by the company National Starch.

(3) partially or completely alkylated and crosslinked polyaminoamides derived from polyamino-amides of general formula III:

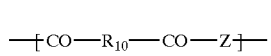

(III)

in which $R_{10}$ represents a divalent radical derived from a saturated dicarboxylic acid, from an aliphatic mono- or dicarboxylic acid comprising an ethylenic double bond, from an ester of a lower alkanol having 1 to 6 carbon atom of these acids, or from a radical derived from the addition of any one of the said acids with a bisprimary or bissecondary amine; and Z denotes a radical of a bisprimary, mono- or bissecondary polyalkylenepolyamine and preferably represents:

a) in the proportions of 60 mol % to 100 mol %, the radical IV

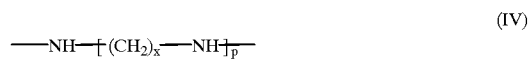

(IV)

where x=2 and p=2 or 3, or else x=3 and p=2 and where this radical derives from diethylenetriamine, triethylenetetraamine, or dipropylenetriamine;

b) in the proportions of 0 mol % to 40 mol %, the above radical (IV), in which x=2 and p=1 and which derives from ethylenediamine, or the radical derived from piperazine:

c) in the proportions of 0 mol % to 20 mol %, the radical —NH—$(CH_2)_6$—NH— derived from hexamethylenediamine, these polyaminoamines being crosslinked by addition of a bifunctional crosslinking agent chosen from epihalohydrins, diepoxides, dianhydrides, or bisunsaturated derivatives, by means of 0.025 mol to 0.35 mol of crosslinking agent per amine group of the polyaminoamide, and alkylated by reaction with acrylic acid, chloracetic acid, or an alkanesultone or their salts.

The saturated carboxylic acids are preferably chosen from acids having 6 to 10 carbon atoms, such as adipic, 2,2,4-trimethyladipic and 2,4,4-trimethyladipic, or terephthalic acid, and the acids comprising an ethylenic double bond, such as, for example, acrylic, methacrylic, or itaconic acids.

The alkanesultones used in the alkylation are preferably propane- or butanesultone. The salts of the alkylating agents are preferably the sodium or potassium salts.

(4) polymers comprising zwitterionic units of formula V:

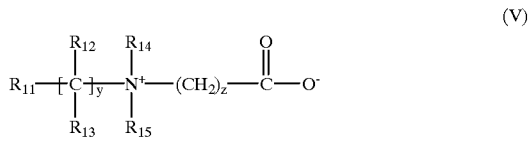

(V)

in which $R_{11}$ denotes a polymerizable unsaturated group, such as an acrylate, methacrylate, acrylamide, or methacrylamide group; y and z represents an integer from 1 to 3; $R_{12}$ and $R_{13}$ are radicals chosen from a hydrogen atom, methyl, ethyl, and propyl; and $R_{14}$ and $R_{15}$ are radicals chosen from a hydrogen atom and an alkyl radical such that the sum of the carbon atoms in $R_{14}$ and $R_{15}$ does not exceed 10.

The polymers comprising such units can also comprise units derived from non-zwitterionic monomers, such as dimethyl- or diethylaminoethyl acrylate or methacrylate, alkyl acrylates or methacrylates, acrylamides or methacrylamides, or vinyl acetate.

Mention may be made, by way of example, of the methyl methacrylate/methyl dimethylcarboxymethylammonioethyl methacrylate copolymer, such as the product sold under the name Diaformer Z301 by the company Sandoz.

(5) polymers derived from chitosan comprising monomer units corresponding to the following formulae:

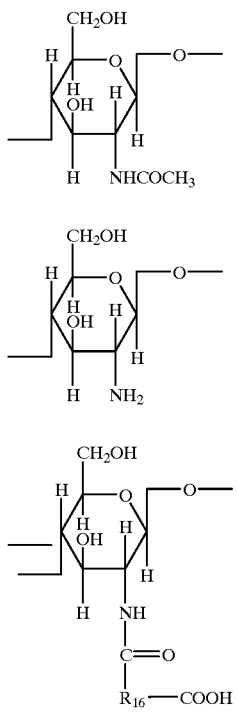

(D)

(E)

(F)

the unit D being present in proportions ranging from 0% to 30%, the unit E in proportions ranging from 5% to 50% and the unit F in proportions ranging from 30% to 90%, it being understood that, in this unit F, $R_{16}$ represents a radical of formula:

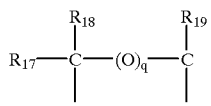

in which, if q=0, $R_{17}$, $R_{18}$, and $R_{19}$, which are identical or different, each represent a hydrogen atom, a methyl, hydroxyl, acetoxy, or amino residue, a monoalkylamine residue or a dialkylamine residue, optionally interrupted by one or more nitrogen atoms and/or optionally substituted by one or more amine, hydroxyl, carboxy, alkylthio, or sulpho groups, or an alkylthio residue in which the alkyl group carries an amino residue, at least one of the $R_{17}$, $R_{18}$, and $R_{19}$ radicals being, in this case, a hydrogen atom; or, if q=1, $R_{17}$, $R_{18}$, and $R_{19}$ each represent a hydrogen atom, and the salts formed by these compounds with bases or acids.

(6) Polymers derived from the N-carboxyalkylation of chitosan, such as the N-(carboxymethyl)chitosan or the N-(carboxybutyl)chitosan sold under the name "Evalsan" by the company Jan Dekker.

(7) Polymers corresponding to the general formula (VI), for example disclosed in French Patent 1,400,366, incorporated herein by reference:

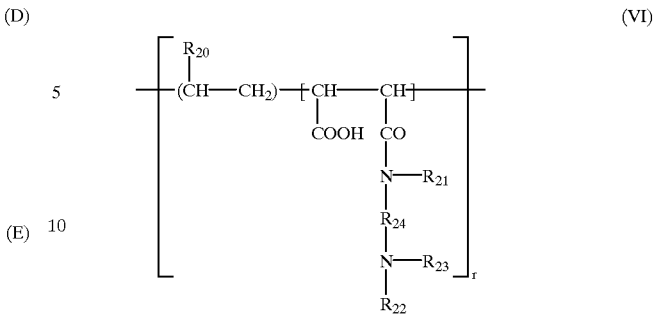

(VI)

in which $R_{20}$ is a radical chosen from a hydrogen atom, a $CH_3O$, $CH_3CH_2O$, and phenyl radical; $R_{21}$ denotes hydrogen or a lower alkyl radical such as methyl or ethyl; $R_{22}$ denotes hydrogen or a lower alkyl radical such as methyl or ethyl; and $R_{23}$ denotes a lower alkyl radical such as methyl or ethyl or a radical corresponding to the formula: $-R_{24}-N(R_{22})_2$, where $R_{24}$ represents a $-CH_2-CH_2-$, $-CH_2-CH_2-CH_2-$, or $-CH_2-CH(CH_3)-$ group and $R_{22}$ having the meanings mentioned above, and the higher homologues of these radicals comprising up to 6 carbon atoms.

(8) Amphoteric fixing polymers of the $-D-X-D-X-$ type chosen from:

a) polymers obtained by reaction of chloracetic acid or sodium chloracetate with compounds comprising at least one unit of formula:

$$-D-X-D-X-D- \qquad (VII)$$

where D denotes a radical

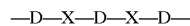

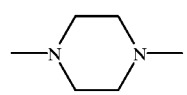

and X denotes the symbol E or E'. E and E', which are identical or different, denote a bivalent radical chosen from straight- and branched-chain alkylene radicals comprising up to 7 carbon atoms in the main chain, which is unsubstituted or substituted by hydroxyl groups and which can additionally comprise oxygen, nitrogen, or sulphur atoms or 1 to 3 aromatic and/or heterocyclic rings; the oxygen, nitrogen, and sulphur atoms being present in the form of ether, thioether, sulphoxide, sulphone, sulphonium, alkylamine or alkenylamine groups, hydroxyl, benzylamine, amine oxide, quaternary ammonium, amide, imide, alcohol, ester, and/or urethane groups.

b) Polymers of formula:

$$-D-X-D-X- \qquad (VII')$$

where D denotes a radical

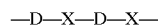

and X denotes the symbol E or E' and E' at least once, where E has the meaning indicated above and E' is a bivalent radical chosen from straight- and branched-chain alkylene radicals having up to 7 carbon atoms in the main chain, which is substituted or unsubstituted by one or more hydroxyl radicals and which comprises one or more nitrogen atoms, the nitrogen atom being substituted by an alkyl chain optionally interrupted by an oxygen atom and necessarily comprising one or more carboxyl functional groups or one or more hydroxyl functional groups and betainized by reaction with chloracetic acid or sodium chloracetate.

(9) (C1–C5)alkyl vinyl ether/maleic anhydride copolymers, which is partially modified by semiamidation with an N,N-dialkylaminoalkylamine, such as N,N-dimethylaminopropylamine, or by semiesterification with an N,N-dialkanolamine. These copolymers can also comprise other vinyl comonomers, such as vinylcaprolactam.

The particularly preferred amphoteric fixing polymers according to the invention are those of the family (3), such as the copolymers with the CTFA name (4$^{th}$ Ed. 1991) of octylacrylamide/acrylates/butylaminoethyl methacrylate copolymer, such as the products sold under the names Amphomer, Amhomer LV 71, or Lovocryl 47 by the company National Starch, and those of the family (4), such as methyl methacrylate/methyl dimethylcarboxymethylammonioethyl methacrylate copolymer, for example sold under the name Diaformer Z301 by the company Sandoz.

The non-ionic fixing polymers which can be used according to the present invention are chosen, for example, from:

vinylpyrrolidone homopolymers;

copolymers of vinylpyrrolidone and of vinyl acetate;

polyalkyloxazolines, such as the polyethyloxazolines provided by the company Dow Chemical under the names PEOX 50 000, PEOX 200 000 and PEOX 500 000;

vinyl acetate homopolymers, such as the product provided under the name Appretan EM by the company Hoechst or the product provided under the name Rhodopas A 012 by the company Rhône-Poulenc;

copolymers of vinyl acetate and of acrylic ester, such as the product provided under the name Rhodopas AD 310 from Rhône-Poulenc;

copolymers of vinyl acetate and of ethylene, such as the product provided under the name Appretan TV by the company Hoechst;

copolymers of vinyl acetate and of maleic ester, for example of dibutyl maleate, such as the product provided under the name Appretan MB Extra by the company Hoechst;

copolymers of polyethylene and of maleic anhydride;

alkyl acrylate homopolymers and alkyl methacrylate homopolymers, such as the product provided under the name Micropearl RQ 750 by the company Matsumoto or the product provided under the name Luhydran A 848 S by the company BASF;

acrylic ester copolymers, such as, for example, copolymers of alkyl acrylates and of alkyl methacrylates, such as the products provided by the company Rohm & Haas under the names Primal AC-261 K and Eudragit NE 30 D, by the company BASF under the names Acronal 601, Luhydran R 8833 or 8845, or by the company Hoechst under the names Appretan N 9213 or N9212;

copolymers of acrylonitrile and of a non-ionic monomer chosen, for example, from butadiene and alkyl (meth) acrylates; mention may be made of the products provided under the names Nipol LX 531 B by the company Nippon Zeon or those provided under the name CJ 0601 B by the company Rohm & Haas;

polyurethanes, such as the products provided under the names Acrysol RM 1020 or Acrysol RM 2020 by the company Rohm & Haas or the products Uraflex XP 401 UZ or Uraflex XP 402 UZ by the company DSM Resins;

copolymers of alkyl acrylate and of urethane, such as the product 8538-33 by the company National Starch;

polyamides, such as the product Estapor LO 11 provided by the company Rhône-Poulenc; and chemically modified or unmodified non-ionic guar gums. The unmodified non-ionic guar gums are, for example, the products sold under the name Vidogum GH 175 by the company Unipectine and under the name Jaguar C by the company Meyhall. The modified non-ionic guar gums, which can be used according to the invention, are preferably modified by $C_1$–$C_6$ hydroxyalkyl groups. Mention may be made, by way of example, of the hydroxymethyl, hydroxyethyl, hydroxypropyl, and hydroxybutyl groups. These guar gums are well known in the state of the art and can, for example, be prepared by reacting the corresponding alkene oxides, such as, for example, propylene oxides, with guar gum, so as to obtain a guar gum modified by hydroxypropyl groups.

Such non-ionic guar gums optionally modified by hydroxyalkyl groups are, for example, sold under the trade names Jaguar HP8, Jaguar HP60, Jaguar HP120, Jaguar DC 293, and Jaguar HP 105 by the company Meyhall or under the name Galactasol 4H4FD2 by the company Aqualon.

The alkyl radicals of the non-ionic fixing polymers have from 1 to 6 carbon atoms, unless otherwise mentioned.

The non-ionic fixing polymer which are very particularly suitable for the preparation of the compositions in accordance with the invention are those chosen from:

vinyllactam copolymers, such as copolymers of vinylpyrrolidone and of vinyl acetate and vinylpyrrolidone/vinyl acetate/vinyl propionate copolymers;

the polyvinylcaprolactam Luviskol Plus (BASF);

vinyl acetate homopolymers, such as Appretan EM (Hoechst) or Rhodopas A 012 (Rhône-Poulenc);

polyalkyloxazolines, such as PEOX 50 000 and PEOX 500 000 (Dow Chemical);

copolymers of vinyl acetate and of acrylic ester, such as Rhodopas AD 310 (Rhône-Poulenc);

copolymers of vinyl acetate and of ethylene, such as Appretan TV (Hoechst);

copolymers of vinyl acetate and of maleic ester, such as Appretan MB Extra (Hoechst);

alkyl acrylate homopolymers and alkyl metacrylate homopolymers, such as Luhydran A 848 S (BASF);

acrylic ester copolymers, such as Primal AC-261 K (Röhm & Haas), Acronal 610 (BASF) or Appretan N 9213 (Hoechst);

copolymers of acrylonitrile and of a non-ionic monomer, such as CJ 0601 B (Röhm & Haas);

polyurethanes, such as Acrysol RM 1020 or Acrysol RM 2020 (Röhm & Haas);

copolymers of alkyl acrylate and of urethane, such as 8538-33 (National Starch); and polyamides, such as Estapor LO 11 (Rhône-Poulenc).

According to the invention, it is also possible to use fixing polymers of grafted silicone type comprising a polysiloxane portion and a portion composed of a non-silicone organic chain, one of the two portions constituting the main chain of the polymer and the other being grafted onto the said main chain. These polymers are disclosed, for example, in Patent Applications EP-A-0,412,704, EP-A-0,412,707, EP-A-0, 640,105, WO 95/00578, EP-A-0,582,152, and WO 93/23009 and U.S. Pat. Nos. 4,693,935, 4,728,571, and 4,972,037 all of which are incorporated herein by reference. These polymers are preferably anionic or non-ionic.

Such polymers are, for example, the copolymers capable of being obtained by radical polymerization from the mixture of monomers composed of:

a) 50% to 90% by weight of tert-butyl acrylate;
b) 0% to 40% by weight of acrylic acid;
c) 5% to 40% by weight of silicone macromer of formula:

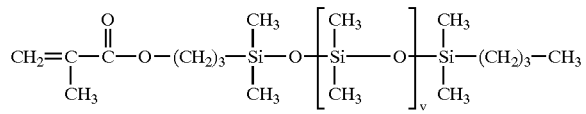

where v is a number ranging from 5 to 700; the percentages by weight being calculated with respect to the total weight of the monomers.

Other examples of grafted silicone polymers are in particular polydimethylsiloxanes (PDMS) on which are grafted, via a connecting link of thiopropylene type, mixed polymer units of the poly(meth)acrylic acid type and of the poly(alkyl (meth)acrylate) type and polydimethylsiloxanes (PDMS) on which are grafted, via a connecting link of thiopropylene type, polymer units of the poly(isobutyl (meth)acrylate) type.

It is also possible to use, as fixing polymers, functionalized or non-functionalized and silicone-comprising or non-silicone-comprising polyurethanes.

The polyurethanes particularly targeted by the present invention are those disclosed in Patents EP 0,751,162, EP 0,637,600, FR 2,743,297, EP 0,648,485, EP 0,656,021, WO 94/03510, and EP 0,619,111, which are incorporated herein by reference.

The non-oxyalkylenated silicone is present in the composition at a relative concentration by weight of greater than 10% by weight with respect to the total weight of the composition, preferably ranging from 15% to 50% by weight and more preferably still from 15% to 30%.

The emulsifying oxyalkylenated silicone is preferably present in the composition at a relative concentration by weight of active material ranging from 0.1% to 10% with respect to the total weight of the composition, more preferably from 0.5% to 5% and more preferably still from 1% to 3%.

The relative concentration by weight of fixing polymer in the composition is advantageously ranging from 0.1 % to 20% by weight with respect to the total weight of the composition and more advantageously still from 0.5% to 10% by weight.

The cosmetically acceptable medium is preferably composed of water or one or more cosmetically acceptable solvents, such as monoalcohols, polyalcohols, glycol ethers, or fatty acid esters, or water/solvent mixtures, these solvents preferably being $C_1$-$C_4$ alcohols.

The compositions of the invention can also, in addition, comprise at least one additive chosen from fatty substances, thickening agents, softeners, moisturizing agents, colorants, fragrances, preservatives, surfactants, proteins, and vitamins.

These additives are optionally present in the composition according to the invention in proportions, which can advantageously range from 0.001% to 20% by weight with respect to the total weight of the composition. The precise amount of each additive depends on its nature and is readily determined by a person skilled in the art and will depend on the hair application chosen.

In particular, a coemulsifier, preferably a non-ionic coemulsifier, of the polysorbate 20 type, or an electrolyte, such as, for example, sodium chloride or magnesium sulphate, and/or emollient agents of polyol type, such as glycerol or propylene glycol, can be added.

In particular, a preservative can be added, for example, products sold under the name Phenonip by the company NIPA and the products sold under the name Germall II by the company ISP.

Of course, a person skilled in the art will take care to choose the optional compounds to be added to the composition according to the invention so that the advantageous properties intrinsically attached to the composition in accordance with the invention are not, or not substantially, detrimentally affected by the envisaged addition.

The compositions of the invention in the form of a water-in-silicone emulsion can be used in the manufacture of numerous hair products, such as, for example, products for fixing and/or retaining the form of the hair, conditioners, such as sheen formulations, or hair care products.

These hair formulations according to the invention will preferably be packaged in tubes or pots.

The invention may be better understood with the help of the following nonlimiting examples, which constitute advantageous embodiments of the compositions in accordance with the invention.

All the amounts are expressed as relative percentages by weight with respect to the total weight of the composition and "a.m." means active material.

The products used in the examples are listed hereinbelow:

| | |
|---|---|
| DC 245 Fluid | Non-oxyalkylenated silicone sold by Dow Corning |
| DC 200 Fluid | Non-oxyalkylenated silicone sold by Dow Corning |
| DC 5225 C | Emulsifying oxyalkylenated silicone sold by Dow Corning |
| DC 556 Fluid | Non-oxyalkylenated silicone sold by Dow Corning |
| DC 2-5185C | Emulsifying oxyalkylenated silicone sold by Dow Corning |
| Montanox 20 | Polysorbate 20 sold by Seppic |
| Luviquat HM 552 | Polyquaternium 16 sold by BASF |
| Luviskol VA 64 P | PVP/VA copolymer sold by BASF |
| Amerhold DR25 | Acrylate copolymer sold by Amerchol |

EXAMPLES

The emulsions hereinbelow in accordance with the present invention are prepared.

| Styling emulsion 1 | |
|---|---|
| DC 245 Fluid (Dow Corning) | 7 |
| DC 5225 C (Dow Corning) | 7 |
| DC 200 Fluid (Dow Corning) | 5 |
| NaCl | 1 |
| Montanox 20 (Seppic) | 0.5 |
| Luviquat HM 552 (BASF) | 2 |
| Luviskol VA 64 P (BASF) | 2 |
| Preservative | q.s. |
| Water | q.s. for 100 |

| Styling emulsion 2 | |
| --- | --- |
| DC 245 Fluid (Dow Corning) | 15 |
| DC 5225 C (Dow Corning) | 10 |
| DC 200 Fluid (Dow Corning) | 15 |
| NaCl | 1 |
| Montanox 20 (Seppic) | 0.5 |
| Amerhold DR 25 (Amerchol) | 16 |
| AMP | 0.35 |
| Preservative | q.s. |
| Water | q.s. for 100 |

| Sheen emulsion 3 (Comparative) | |
| --- | --- |
| DC 245 Fluid (Dow Corning) | 7 |
| DC 5225 C (Dow Corning) | 10 |
| Propylene glycol | 38 |
| NaCl | 1 |
| Luviskol VA 64 P (BASF) | 0.1 |
| Ethanol | 11.2 |
| Preservative | q.s. |
| Water | q.s. for 100 |

| Sheen emulsion 4 | |
| --- | --- |
| DC 245 Fluid (Dow Corning) | 10 |
| DC 2-5185C (Dow Corning) | 5 |
| DC 556 Fluid (Dow Corning) | 15 |
| NaCl | 1 |
| Montanox 20 (Seppic) | 1 |
| Aristoflex A (Clariant) | 3.33 |
| AMP | 0.25 |
| Preservative | q.s. |
| Water | q.s. for 100 |

| Care emulsion 5 | |
| --- | --- |
| DC 245 Fluid (Dow Corning) | 5 |
| DC 5225 C (Dow Corning) | 7 |
| DC 1501 Fluid (Dow Corning) | 10 |
| NaCl | 1 |
| Montanox 20 (Seppic) | 0.5 |
| DC 2 1388 Emulsion | 10 |
| Luviskol VA 64 P | 0.1 |
| Preservative | q.s. |
| Water | q.s. for 100 |

What is claimed is:

1. A hair cosmetic composition in the form of a water-in-silicone emulsion comprising in a cosmetically acceptable medium:
   (i) at least one non-oxyalkylenated silicone chosen from linear and cyclic silicones, wherein the total non-oxyalkylenated silicone is more than 10% by weight with respect to the total weight of the composition;
   (ii) at least one emulsifying oxyalkylenated silicone; and
   (iii) at least one fixing polymer chosen from anionic, cationic, amphoteric, and non-ionic fixing polymers.

2. The composition according to claim 1, wherein the concentration of the non-oxyalkylenated silicone ranges from 15% to 50% by weight with respect to the total weight of the composition.

3. The composition according to claim 1, wherein the concentration of the non-oxyalkylenated silicone ranges from 15% to 30% by weight with respect to the total weight of the composition.

4. The composition according to claim 1, wherein the emulsifying oxyalkylenated silicone comprises an active material, said active material having a relative concentration ranging from 0.1% to 10% by weight with respect to the total weight of the composition.

5. The composition according to claim 1, wherein the emulsifying oxyalkylenated silicone comprises an active material, said active material having a relative concentration ranging from 0.5% to 5% by weight with respect to the total weight of the composition.

6. The composition according to claim 1, wherein the emulsifying oxyalkylenated silicone comprises an active material, said active material having a relative concentration ranging from 1% to 3% by weight with respect to the total weight of the composition.

7. The composition according to claim 1, wherein the concentration of the fixing polymer ranges from 0.1% to 20% by weight with respect to the total weight of the composition.

8. The composition according to claim 1, wherein the concentration of the fixing polymer ranges from 0.5% to 10% by weight with respect to the total weight of the composition.

9. The composition according to claim 1, further comprising a coemulsifier.

10. The composition according to claim 1, further comprising an electrolyte.

11. The composition according to claim 1, wherein the fixing polymer is an anionic fixing polymer chosen from
   (a) polymers comprising carboxyl units derived from unsaturated carboxylic monoacid or diacid monomers of the formula:

$$R_7 \diagdown_{C=C} \diagup^{(A)_{\overline{n}}-COOH}_{R_9} \atop R_8 \qquad \qquad \qquad \qquad \text{(II)}$$

where n is an integer from 0 to 10; A denotes a methylene group and when n is greater than 1, each A is represented by —LCH$_2$—, where L is a heteroatom; $R_7$ is chosen from a hydrogen atom, a phenyl group, and a benzyl group; $R_8$ is chosen from a hydrogen atom, a lower alkyl, and a carboxyl group; and $R_9$ is chosen from a hydrogen atom, a lower alkyl group, a —CH$_2$—COOH, a phenyl group, and a benzyl group; and
   (b) polymers comprising units derived from sulphonic acid.

12. The composition according to claim 11, wherein said heteroatom is chosen from oxygen and sulphur atoms.

13. The composition according to claim 11, wherein said units derived from sulphonic acid are chosen from vinylsulphonic, styrenesulphonic and acrylamidoalkylsulphonic units.

14. The composition according to claim 1, wherein the fixing polymer is an amphoteric fixing polymer chosen from polymers comprising units derived from:
   (a) at least one monomer chosen from acrylamides and methacrylamides substituted on the nitrogen by an alkyl radical;
   (b) at least one acidic comonomer comprising one or more reactive carboxyl groups; and
   (c) at least one basic comonomer.

15. The composition according to claim 14, wherein the basic comonomer is chosen from esters comprising primary, secondary, tertiary and quaternary amine substituents of acrylic and methacrylic acids and the quaternization product of dimethylaminoethyl methacrylate with dimethyl or diethyl sulphate.

16. The composition according to claim 1, wherein the fixing polymer is an amphoteric fixing polymer chosen from partially or completely alkylated and crosslinked polyaminoamides derived from polyamino-amides of general formula III:

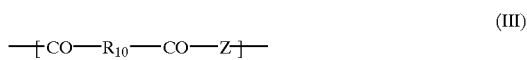

(III)

in which $R_{10}$ represents a divalent radical chosen from divalent radicals derived from a saturated dicarboxylic acid, from an aliphatic mono- or dicarboxylic acid comprising an ethylenic double bond, from an ester of a lower alkanol having 1 to 6 carbon atom of these acids, and from radicals derived from the addition of any one of the said acids with a bisprimary or bissecondary amine; and Z denotes a radical of a bisprimary, mono- or bissecondary polyalkylenepolyamine.

17. The composition according to claim 1, wherein the fixing polymer is an amphoteric fixing polymer chosen from polymers comprising zwitterionic units of the formula V:

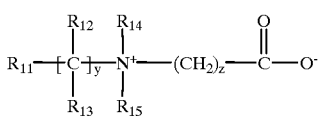

(V)

where $R_{11}$ denotes a polymerizable unsaturated group; y and z denote an integer from 1 to 3; $R_{12}$ and $R_{13}$ are radicals chosen from a hydrogen atom, methyl, ethyl, and propyl; and $R_{14}$ and $R_{15}$ are radicals chosen from a hydrogen atom and an alkyl radical such that the sum of the carbon atoms in $R_{14}$ and $R_{15}$ does not exceed 10.

18. The composition according to claim 1, wherein the fixing polymer is a non-ionic fixing polymer chosen from vinylpyrrolidone homopolymers, copolymers of vinylpyrrolidone and of vintl acetate, polyalkyloxazolines, vinyl acetate homopolymers, copolymers of vinyl acetate and of acrylic ester, copolymers of vinyl acetate and of ethylene; copolymers of vinyl acetate and of maleic ester, copolymers of polyethylene and of maleic anhydride, alkyl acrylate homopolymers, alkyl methacrylate homopolymers, acrylic ester copolymers, copolymers of acrylonitrile and of a non-ionic monomer, polyurethanes, copolymers of alkyl acrylate and of urethane, polyamides, and chemically modified or unmodified non-ionic guar gums.

19. The composition according to claim 18, wherein the acrylic ester copolymers are chosen from copolymers of alkyl acrylates and of alkyl methacrylates.

20. The composition according to claim 18, wherein the non-ionic monomer of the copolymers of acrylonitrile and of a non-ionic monomer is chosen from butadiene and alkyl (meth)acrylates.

21. The composition according to claim 1, wherein the fixing polymer is a cationic fixing polymer chosen from the copolymer of acrylamide and of dimethylaminoethyl methacrylate quaternized with dimethyl sulphate, copolymers of acrylamide and of methacryloyloxyethyltrimethylammonium chloride, the copolymer of acrylamide and of methacryloyloxyethyltrimethylammonium methyl sulphate, optionally quaternized vinylpyrrolidone/dialkylaminoalkyl (meth)acrylate copolymers, dimethylaminoethyl methacrylate/vinyl-caprolactam/vinylpyrrolidone terpolymer, the quaternized dimethylaminopropyl methacrylamide/vinylpyrrolidone copolymer, quaternized polysaccharides, quaternary copolymers of vinylpyrrolidone and of vinylimidazole, chitosans and their salts, and cationic cellulose derivatives.

22. The composition according to claim 21, wherein the quaternized polysaccharides are guar gums including cationic trialkylammonium groups.

23. The composition according to claim 1, wherein the fixing polymer is a functionalized or non-functionalized and silicone-comprising or non-silicone-comprising polyurethane.

24. The composition according to claim 1, wherein the fixing polymer is a polymer of grafted silicone type comprising a polysiloxane portion and a non-silicone organic chain portion, wherein either of the two portions constitutes a main chain of the polymer and the other is grafted onto said main chain.

25. The composition according to claim 1, wherein the emulsifying oxyalkylenated silicones are chosen from the compounds of general formula (I):

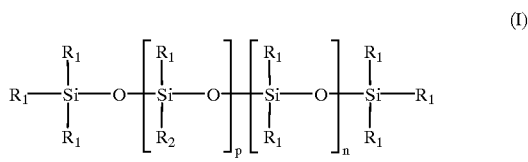

(I)

wherein $R_1$, in each instance is identical or different and is a radical chosen from a hydrogen atom, a linear or branched $C_1$–$C_{30}$ alkyl radical, and a phenyl radical; $R_2$ in each instance is identical or different and represents —$(C_xH_{2x})$—$(OC_2H_4)_a$—$(OC_3H_6)_b$—$OR_3$; $R_3$ in each instance is identical or different and is a radical chosen from a hydrogen atom, linear or branched alkyl radical having from 1 to 12 carbon atoms, and a linear or branched acyl radical having from 2 to 12 carbon atoms; n varies from 0 to 1000; p varies from 1 to 8; a varies from 0 to 50; b varies from 0 to 50; a+b is greater than or equal to 1; x varies from 1 to 5; and the number-average molecular weight of said silicone being greater than or equal to 15,000 and preferably ranging from 25,000 to 75,000.

26. The composition according to claim 1, further comprising at least one cosmetic additive chosen from fatty substances, thickening agents, softeners, moisturizing agents, colorants, fragrances, preservatives, surfactants, proteins, and vitamins.

27. The composition according to claim 1, wherein the composition is packaged in the form of tubes or pots.

28. A hair cosmetic process comprising the step of applying the composition according to claim 1 to the hair.

29. The process according to claim 28, wherein the composition fixes and/or retains the form of the hair.

30. A method for the manufacture of a hair product comprising the inclusion of a hair cosmetic composition according to claim 1 in the hair product.

31. The method according to claim 30, wherein the hair product retains the form of and/or fixes the hair.

32. The method according to claim 30, wherein the hair product conditions the hair.

33. The method according to claim 32, wherein the hair product is a sheen product.

34. The method according to claim 30, wherein the hair product is a hair care product.

35. A hair product for retaining the form of and/or fixing the hair, comprising a composition in the form of a water-in-silicone emulsion comprising in a cosmetically acceptable medium:

(i) at least one non-oxyalkylenated silicone chosen from linear and cyclic silicones, wherein the total non-oxyalkylenated silicone is more than 10% by weight with respect to the total weight of the composition;

(ii) at least one emulsifying oxyalkylenated silicone; and (iii) at least one fixing polymer chosen from anionic, cationic, amphoteric, and non-ionic fixing polymers.

* * * * *